United States Patent [19]

Shaw

[11] Patent Number: 5,162,585
[45] Date of Patent: Nov. 10, 1992

[54] PREPARATION OF DIHYDROXY BIS-SULFIDES

[75] Inventor: James E. Shaw, Bartlesville, Okla.

[73] Assignee: Phillips Petroleum Company, Bartlesville, Okla.

[21] Appl. No.: 681,305

[22] Filed: Apr. 8, 1991

[51] Int. Cl.$^5$ .................. C07C 319/24; C07C 319/28
[52] U.S. Cl. ........................................ 568/46; 568/19; 568/38; 568/50
[58] Field of Search ............... 568/46, 19, 38, 50

[56] References Cited

U.S. PATENT DOCUMENTS 4,449,004  5/1984  Degani et al. ..................... 568/38

FOREIGN PATENT DOCUMENTS 9125328  9/1973  Japan ..................... 568/38

OTHER PUBLICATIONS

R. Rosen and E. Reid, "Sesqui–mustard Gas or Bis–β–chloroethyl Ether of Ethylene Dithio-glycol", 1922, pp. 634–636, J. Amer. Chem. Soc. vol. 44 Chem. Abstr. 104:177577k (1986) Discloses the use of 1,8-Dihydroxy-3,6-dithiaoctane in the preparation of AgBr emulsion.

*Primary Examiner*—Marianne Cintins
*Assistant Examiner*—John D. Peabody, III
*Attorney, Agent, or Firm*—Lucas K. Shay

[57] ABSTRACT

A process for preparing a dihydroxy bis-sulfide is disclosed, wherein a thiolate salt, a dihaloalkane, an ether solvent that is partially soluble in water and is substantially nonreactive with either said thiolate salt or said dehaloalkane; and water are contacted under reaction conditions sufficient to synthesize a dihydroxy bis-sulfide; to subsequently recover a dihydroxy bis-sulfide.

18 Claims, No Drawings

PREPARATION OF DIHYDROXY BIS-SULFIDES

FIELD OF THE INVENTION

This invention relates to the preparation of dihydroxy bis-sulfides.

BACKGROUND OF THE INVENTION

Dihydroxy bis-sulfides are sulfur-containing organic compounds having many uses. One desirable feature of these compounds is their emulsifying capability. Dihydroxy bis-sulfide compounds may be used as intermediates for preparing fatty acid esters, as monomers for polysulfide rubbers, as cross-linking agents for polyesters and polyurethanes, as lubricant additives, and as emulsifying agents for photographic silver halide systems.

The prior art discloses preparing dihydroxy bis-sulfides by a reaction of sodium salt of monothioglycol with ethylene bromide and by a reaction of ethylene chlorohydrin with the sodium salt of ethylene dithioglycol, as described in J. Amer. Chem. Soc., Vol. 44, p. 634-636 (1922). These processes, however, produce a low purity, low yield bis-sulfide product.

Alternative processes for preparing a higher yield of dihydroxy bis-sulfide compounds are desirable, especially those processes providing a high purity, high yield product. Further, it would be desirable if a process could be developed where the product could be easily isolated from the reaction mixture.

SUMMARY OF THE INVENTION

It is, therefore, an object of my invention to provide an alternative, novel process for preparing dihydroxy bis-sulfide compounds.

It is a further object of my invention to provide a process for producing dihydroxy bis-sulfide compounds of an acceptable purity level.

It is yet another object of my invention to provide a readily controllable process for preparing a dihydroxy bis-sulfide compound in high yield.

It is still another object of my invention to provide a process allowing for the easy recovery of a dihydroxy bis-sulfide compound from the reaction mixture.

According to my invention, a process for preparing a dihydroxy bis-sulfide is provided which comprises (a) contacting a thiolate salt, a dihaloalkane, water, and at least one organic solvent which is partially soluble in the aqueous phase of reaction mixture and is substantially nonreactive with the thiolate salt or the dihaloalkane, under reaction conditions sufficient to produce said dihydroxy bis-sulfide.

DETAILED DESCRIPTION

I have discovered that when an organic solvent is included in the reaction mixture comprising a thiolate salt, a dihaloalkane and water, a highly pure dihydroxy bis-sulfide can be recovered in a high yield.

The dihydroxy bis-sulfide formed can be represented by the general formula $HOR(R'')SR'SR(R'')OH$ wherein R is an alkylene radical having 2 to 4 carbon atoms;
R' is an alkylene radical having 1 to 20 carbon atoms; and
R'' is hydrogen or an alkyl radical having 1 to 16 carbon atoms.

The thiolate salt employed has the general formula $[HOR(R'')S]_nM$, wherein R is an alkylene radical as defined above, R'' is hydrogen or an alkyl radical as defined above, M is a Group I metal of the Periodic Table, a Group II metal of the Periodic Table or an ammonium ion, and n is 1 when M is a Group I metal of the Periodic Table or an ammonium ion and 2 when M is a Group II metal of the Periodic Table. Preferably M is selected from the group consisting of lithium, sodium, potassium, cesium, magnesium, and calcium. Preferred thiolate salts are sodium or potassium salts. Most preferred are sodium salts of hydroxy thiols formed as described in the next paragraph.

The thiolate salt reactant component can be placed in the reaction mixture as a thiolate salt or, alternatively, can be formed in the reaction mixture by neutralizing a hydroxy thiol with a base prior to addition of the dihaloalkane.

At the present time, for purposes of availability, it is preferred that the thiolate salt is formed in the reaction mixture prior to addition of the dihaloalkane by reacting a hydroxy thiol with a base. More preferably the thiolate salt is formed by reacting a hydroxy thiol selected from the group consisting of 2-mercaptoethanol, 3-mercapto-1-propanol, 1-mercapto-2-propanol, and 1-mercapto-2-butanol with a base. The base is a hydroxide or carbonate of a Group I or Group II metal or ammonium hydroxide. Exemplary bases are sodium hydroxide, potassium hydroxide, lithium hydroxide, cesium hydroxide, calcium hydroxide, magnesium hydroxide, ammonium hydroxide, sodium carbonate, potassium carbonate, and mixtures thereof. The base reacts with the thiol group of the hydroxy thiol and the hydroxy group is substantially unaffected by the base. Most preferably, the thiolate salt is formed in the reaction mixture prior to addition of the dihaloalkane by reacting a 2-mercaptoethanol with a sodium hydroxide.

In accordance with my invention, the dihaloalkane component employed has a general formula of $XR'X$, wherein each X is a halogen independently selected from the group consisting of fluorine, chlorine, bromine and iodine; and R' is an alkylene radical having 1 to 20 carbon atoms, as previously defined. More preferably, the dihaloalkane is selected from the group consisting of dichloromethane, 1,2-dichloroethane, 1,3-dichloropropane, bromochloromethane, dibromomethane, 1,2-dibromoethane, 1-bromo-3-chloropropane, and 1,8-dichlorooctane. Most preferably 1,2-dichloroethane is employed.

The proper selection of a suitable organic solvent is important to the advantages gained by my inventive process, i.e. high purity, high yield product and increased reaction rate. In selecting a suitable organic solvent, I have found that the organic solvent should be partially soluble in aqueous phase of the reaction mixture. Generally, the solubility will be about 1 to about 250 g/l, preferably about 5 to about 100 g/l, and most preferably about 10 to about 50 g/l and should be substantially nonreactive with the thiolate salt or the dihaloalkane. Preferably the solvent is substantially soluble in the organic phase. Ionic reagents such as thiolate salts have some solubility in the organic solvent generally about 10 to about 500 g/l, preferably about 50 to about 300 g/l, and most preferably about 100 to about 200 g/l.

I have found that at least one oxygenated hydrocarbon selected from the group consisting of ethers having 2 to about 6 carbon atoms and alcohols having 1 to about 5 carbon atoms may be employed as the organic solvent. Preferably the organic solvent is an ether or diether selected from the group consisting of tetrahydrofuran, dioxane, 1,2-dimethoxyethane, 1,2-diethoxyethane, 2-methoxyethanol, tetrahydropyran, diethylether, dipropylether, and mixtures thereof. Most preferably tetrahydrofuran is employed as the organic solvent component.

The organic solvent can generally be employed in the reaction mixture in the beginning of the reaction, but it is preferably added immediately prior to the addition of the dihaloalkane. The solvent should be in the range of 5–90% (volume/volume), preferably 5–70%, of the total reaction mixture.

Water is also included in the reaction mixture. Water should be present at the start of the reaction in the range of about 5–70% (volume/volume), preferably about 10–60%, of total reaction mixture.

The dihydroxy bis-sulfide compounds produced by this invention, for example, include 2,4-dithia-1,5-pentanediol, 2,5-dithia-1,6-hexanediol, 2,6-dithia-1,7-heptanediol, 2,7-dithia-1,8-octanediol, 2,8-dithia-1,9-nonanediol, 2,9-dithia-1,10-decanediol, 2,11-dithia-1,12-dodecanediol, 2,15-dithia-1,16-hexadecanediol, 2,21-dithia-1,22-doeicasanediol, 3,5-dithia-1,7-heptanediol, 3,6-dithia-1,8-octanediol, 3,8-dithia-1,10-decanediol, 3,10-dithia-1,8-dodecanediol, 3,13-dithia-1,15-pentadecanediol, 3,18-dithia-1,20-eicosanediol, 4,6-dithia-1,9-nonanediol, 4,7-dithia-1,10-decanediol, 4,11-dithia-1,14-tetradecanediol, 4,15-dithia-1,18-octadecanediol, 4,19-dithia-1,22-dodeicosanediol, 5,7-dithia-1,11-undecanediol, 5,9-dithia-1,13-tridecanediol, 5,13-dithia-1,17-heptadecanediol, 5,17-dithia-1,21-uneicosanediol, 1,8-dimethyl-3,6-dithia-1,8-octanediol, and the like.

The reaction can be carried out in any appropriate manner such as continuous or batch reactions known to those skilled in the art. An embodiment of my invention comprises dissolving a base in water wherein the mole ratio of water to the base is 5 to 30, preferably 10 to 20 followed by addition of a hydroxy thiol wherein the mole ratio of the hydroxy thiol to the base is about 2.5 to about 3.5, preferably about 2.8 to about 3.2, and an organic solvent wherein the mole ratio of the solvent to the base is 0.01 to 20, preferably 0.5 to 10, and most preferably 1 to 5 to the base-solution to prepare a thiolate salt solution. After heating to 40° to 100° C. preferably 50° to 80° C., a dihalide is added slowly so as to maintain the reaction temperature in the range described above wherein the mole ratio of the dihalide to the base is 0.4 to 0.6, preferably about 0.5. The reaction mixture is then refluxed for 1 to 10, preferably 3–8 hours at 40° to 100° C., preferably 50° to 90° C., most preferably 60° to 80° C. while stirring.

Generally the reaction can be run without agitation. However, in order to increase the reaction rate, a suitable agitation such as stirring is desirable.

The reaction mixture, upon completion of the reaction, is transferred to a suitable separation means, such as separatory funnel or centrifuge, for product separation. For example, when the reaction mixture transferred to a separatory funnel, phase separation occurs giving organic and aqueous layers. The aqueous layer is formed on the bottom and can be separated and can be recycled, if necessary, to further separate the desired product and to recover the unused reactants and other salts. The top, organic layer contains substantially all of the product, hydroxy-bis-sulfide that may be recovered and purified. However, the product in the organic solvent may be used without further recovery.

The organic solvent can be removed and recovered, if necessary, for reuse, from the product by any suitable means, for example, rotary evaporation. The dihydroxy bis-sulfide product can be isolated and recovered, generally as a hard, white solid product.

The following non-limiting examples are provided to further illustrate the practice of my invention.

COMPARATIVE EXAMPLE I

This example illustrates a dihydroxy bis-sulfide prepared with a phase transfer catalyst without the use of an organic solvent.

To a 2 liter, 3 necked flask fitted with a thermowell, magnetic stirrer, addition funnel, condenser, and $N_2$ inlet was added 10 moles of sodium hydroxide and 111 moles of water. After the sodium hydroxide was dissolved, 10 moles of 2-mercaptoethanol was added slowly from the addition funnel. After heating to 60° C., 5 moles of 1,2-dichloroethane was added slowly to the reaction mixture. The reaction mixture was rapidly stirred during the addition. There was no evidence of reaction. No heat was produced. The reaction mixture was heated at 60°–90° C. for 2 hours with stirring. The reaction proceeded very slowly, so a small amount (20 g) of a quaternary ammonium salt (methyltrialkyl ($C_8$–$C_{10}$) ammonium chloride) phase transfer catalyst was added to increase the reaction rate. The reaction mixture was heated to 81° C. for 3 hours with rapid stirring.

The reaction mixture was then transferred to a separatory funnel for phase separation but the mixture did not phase separate properly. This was due to incomplete reaction as shown by the presence of unreacted 1,2-dichloroethane. No product was collected.

COMPARATIVE EXAMPLE II

Five reaction mixtures were prepared in the manner shown in Comparative Example I with the exception that 100 g of the quaternary ammonium salt phase transfer agent was added prior to the addition of the 1,2-dichloroethane. The 1,2-dichloroethane was added slowly at 60° C. so the reaction mixture stayed at 60°–78° C. The reaction mixture was rapidly stirred during the addition. After the addition was complete, the reaction mixture was refluxed (80°–82° C.) for 2–4.5 hours.

The reaction mixture was transferred to a separatory funnel for phase separation. The mixture was kept hot so that solid would not form. After phase separation, the top layer was removed and allowed to solidify giving crude product, 3,6-dithia-1,8-octanediol as a white solid. The five experiments gave 866, 901, 917, 901, and 890 grams of crude product which represented yields, based on total weight of 1,2-dichloroethane and 2-mercapto-ethanol of 95, 99, 101, 99, and 98%, respectively, but analysis by gas chromatography (HP 5880 Gas Chromotograph; 2% OV-101 column, 20 in × ⅛ in stainless steel; 50° C. then programmed at 15° C./min. to 250° C.) showed the products were quite impure containing, on the average, only 67% 3,6-dithia-1,8-octanediol.

EXAMPLE I

This example illustrates that my inventive process produces a dihydroxy bis-sulfide in good yield.

As in Comparative Examples I and II, a 2 liter, 3-necked flask fitted with a thermowell, magnetic stirrer, addition funnel, condenser, and $N_2$ inlet was employed.

To the flask was added 3 moles of sodium hydroxide and 33.3 moles of water. After the sodium hydroxide was dissolved, 3 moles of 2-mercaptoethanol was added slowly from the addition funnel. Then 3.34 moles of tetrahydrofuran as the organic solvent was added. After heating to 60° C., 148.5 g of 1,2-dichloroethane was added dropwise at such a rate that the temperature stayed at 60° C. The reaction mixture was rapidly stirred during the addition. After addition of the 1,2-dichloroethane, the reaction mixture was refluxed (67°-70° C.) for 6 hours. Stirring was continued during refluxing.

After cooling, the reaction mixture was transferred to a separatory funnel for phase separation. The top layer contained the desired product and was evaporated on a rotary evaporator to remove the organic solvent. This gave 260 g of 3,6-dithia-1,8-octanediol as a white solid. This represented a yield of 94% based on total weight of 1,2-dichloroethane and 2-mercaptoethanol. Gas chromatography analysis of the solid indicated a purity of greater than 98%.

EXAMPLE II

Four runs were carried out in a 5 liter flask equipped as the flask described in Example I, with the exception that each of the reaction mixtures were larger because increased quantities of the components were employed. To the flask was added 10 moles of sodium hydroxide and 111 moles of water. After the sodium hydroxide was dissolved, 10 moles of 2-mercaptoethanol was added slowly from the addition funnel. Then 1000 ml of tetrahydrofuran was added. After heating to 60° C., 5 moles of 1,2-dichloroethane was added dropwise at such a rate that the temperature would stay at 60° C. The reaction mixture was rapidly stirred during the addition. After the addition was complete, the reaction mixture was refluxed at 67°-70° C. for 4-5 hours. Stirring was continued during refluxing.

After cooling, the reaction mixture from each of 4 identical experiments, was transferred to a separatory funnel for phase separation. The top layers from the 4 experiments were combined and evaporated on a rotary evaporator to remove tetrahydrofuran solvent. This gave 3337 g of 3,6-dithia-1,8-octanediol as a white solid. This represented an average yield for the 4 runs of 92%. GC analysis of the product indicated a purity of greater than 98%.

The results of Examples I and II demonstrate that my inventive use of a suitable organic solvent greatly improves the yield of the product and the purity of the product over the reactions without using an organic solvent described in Comparative Examples I and II.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A process for preparing a dihydroxy bis-sulfide compound comprising: contacting a thiolate salt, a dihaloalkane, at least one ether solvent, and water under reaction conditions sufficient to synthesize a dihydroxy bis-sulfide compound.

2. A process according to claim 1 comprising additionally recovering said dihydroxy bis-sulfide compound.

3. A process according to claim 1 wherein said dihydroxy bis-sulfide compound has the formula of HOR(R")SR'SR(R")OH wherein R is an alkylene radical having 2 to 4 carbon atoms, R' is an alkylene radical having 1 to 20 carbon atoms and R" is hydrogen or an alkyl radical having 1 to 16 carbon atoms.

4. A process according to claim 1 wherein said thiolate salt has the formula of $[HOR(R")S]_nM$, wherein R is an alkylene radical having 2 to 4 carbon atoms; R" is hydrogen or an alkyl radical having 1 to 16 carbon atoms; M is selected from the group consisting of metals of Group I and Group II of the Periodic Table and ammonium ion; and n is 1 when M is a Group I metal or ammonium ion and is 2 when M is a Group II metal.

5. A process according to claim 4 wherein said thiolate salt is formed in a reaction mixture prior to addition of said dihaloalkane and said ether solvent by reacting a hydroxy thiol with a base.

6. A process according to claim 5 wherein said hydroxy thiol is selected from the group consisting of 2-mercaptoethanol, 3-mercapto-1-propanol, 1-mercapto-2-propanol, and 1-mercapto-2-butanol and said base is selected from the group consisting of sodium hydroxide, potassium hydroxide, lithium hydroxide, cesium hydroxide, calcium hydroxide, magnesium hydroxide, sodium carbonate, potassium carbonate, ammonium hydroxide, and mixtures thereof.

7. A process according to claim 6 wherein said hydroxy thiol is 2-mercaptoethanol and said base is sodium hydroxide.

8. A process according to claim 1 wherein said dihaloalkane is represented by a formula XR'X wherein each X is a halogen selected from the group consisting of fluorine, chlorine, bromine, and iodine; and R' is an alkylene radical having 1 to 20 carbon atoms.

9. A process according to claim 8 wherein said dihaloalkane is selected from the group consisting of dichloromethane, 1,2-dichloroethane, 1,3-dichloropropane, bromochloromethane, dibromomethane, 1,2-dibromoethane, 1-bromo-3-chloropropane, and 1,8-dichlorooctane.

10. A process according to claim 9 wherein said dihaloalkane is 1,2-dichloroethane.

11. A process according to claim 5 wherein said ether solvent is selected from the group consisting of tetrahydrofuran, dioxane, diethyl ether, dipropyl ether, 1,2-dimethoxyethane, and mixtures thereof.

12. A process according to claim 11 wherein said ether solvent is tetrahydrofuran.

13. A process according to claim 1 wherein:
said thiolate salt has the formula of $[HOR(R")S]_nM$ wherein R is an alkylene radical having 2 to 4 carbon atoms; R" is hydrogen or an alkyl radical having 1 to 16 carbon atoms; M is a metal selected from the group consisting of lithium, sodium, potassium, cesium, magnesium, and calcium; and is formed in a reaction mixture prior to addition of said dihaloalkane and said solvent by reacting a hydroxy thiol with a base, and n is 1 when M is a Group I metal or an ammonium ion and 2 when M is a Group II metal;
said dihaloalkane is represented by a formula XR'X wherein X is a halogen selected from the group consisting of fluorine, chlorine, bromine, and iodine; and R' is an alkylene radical having 1 to 20 carbon atoms; and
said ether solvent selected from the group consisting of ethers having 2 to about 6 carbon atoms.

14. A process according to claim 13 wherein said hydroxy thiol is selected from the group consisting of 2-mercaptoethanol, 3-mercapto-1-propanol, 1-mercapto-2-propanol, and 1-mercapto-2-butanol; said base is selected from the group consisting of sodium hydroxide, potassium hydroxide, lithium hydroxide, cesium hydroxide, magnesium hydroxide sodium carbonate, potassium carbonate, ammonium hydroxide, and mixtures thereof; said dihaloalkane is selected from the group consisting of dichloromethane, 1,2-dichloroethane, 1,3-dichloropropane, bromochloromethane, dibromomethane, 1,2-dibromoethane, 1-bromo-3-chloropropane, 1,8-dichlorooctane and mixtures thereof; and said organic solvent is selected from the group consisting of tetrahydrofuran, dioxane, 1,2-dimethoxyethane, diethyl ether, dipropylether and mixtures thereof.

15. A process according to claim 14 wherein said hydroxy thiol is 2-mercaptoethanol; said base is sodium hydroxide; said dihaloalkane is 1,2-dichloroethane; said solvent is tetrahydrofuran; and said dihydroxy bis-sulfide compound is 3,6-dithia-1,8-octanediol.

16. A process for preparing a hydroxy bis-disulfide compound comprising:
   (a) dissolving a base in water wherein the mole ratio of said water to said base is 5 to 30 whereby a basic solution is formed;
   (b) adding a hydroxy thiol wherein the mole ratio of said hydroxy thiol to said base is about 2.5 to about 3.5 and an organic solvent to said basic solution wherein the mole ratio of said organic solvent to said base is about 0.01 to about 20 whereby a thiolate salt solution is formed;
   (c) stirring said thiolate salt solution;
   (d) heating said thiolate salt solution to a temperature range of about 40° to about 100° C.;
   (e) adding said dihaloalkane so as to maintain the temperature of said thiolate salt solution in said temperature range wherein the mole ratio of said dihaloalkane to said base is about 0.4 to about 0.6 whereby a reaction mixture is formed;
   (f) refluxing said reaction mixture for 1 to 10 hours at 40° to 100° C.;
   (g) separating said hydroxy bis-sulfide containing phase from said reaction mixture; and
   (h) removing said organic solvent from said hydroxy bis-sulfide containing phase and recovering said hydroxy bis-sulfide.

17. A process according to claim 16 wherein:
said dihydroxy bis-sulfide compound has the formula of HOR(R")SR'SR(R")OH wherein R is an alkylene radical having 2 to 4 carbon atoms, R' is an alkylene radical having 1 to 20 carbon atoms and R" is hydrogen or an alkyl radical having 1 to 16 carbon atoms;

said thiolate salt has the formula of $[HOR(R")S]_nM$, wherein R is an alkylene radical having 2 to 4 carbon atoms; R" is hydrogen or an alkyl radical having 1 to 16 carbon atoms; M is selected from the group consisting of metals of Group I and Group II of the Periodic Table and ammonium ion; and n is 1 when M is a Group I metal or ammonium ion and is 2 when M is a Group II metal;

said hydroxy thiol is selected from the group consisting of 2-mercaptoethanol, 3-mercapto-1-propanol, 1-mercapto-2-propanol, and 1-mercapto-2-butanol and said base is selected from the group consisting of sodium hydroxide, potassium hydroxide, lithium hydroxide, cesium hydroxide, calcium hydroxide, magnesium hydroxide, sodium carbonate, potassium carbonate, ammonium hydroxide, and mixtures thereof;

said dihaloalkane is represented by a formula XR'X wherein each X is a halogen selected from the group consisting of fluorine, chlorine, bromine, and iodine; and R' is an alkylene radical having 1 to 20 carbon atoms; and said organic solvent is selected from the group consisting of tetrahydrofuran, dioxane, diethyl ether, dipropyl ether, 1,2-dimethoxyethane, and mixtures thereof.

18. A process according to claim 17 wherein said separating is carried out by phase separation and said removing is carried out by rotary evaporation.

* * * * *